United States Patent [19]
Woodward

[11] Patent Number: 5,458,305
[45] Date of Patent: Oct. 17, 1995

[54] PORTABLE INTRAVENOUS SUPPORT STAND

[76] Inventor: John Woodward, 460 Flagstaff, Hoffman Estates, Ill. 60194

[21] Appl. No.: 62,269

[22] Filed: May 17, 1993

[51] Int. Cl.⁶ ........................................... F16L 3/00
[52] U.S. Cl. ................ 248/121; 248/412; 248/188; 248/188.8
[58] Field of Search ................... 248/411, 412, 248/121, 176, 177, 188, 188.1, 188.8, 188.7, 188.5

[56] References Cited

U.S. PATENT DOCUMENTS

| | | | |
|---|---|---|---|
| D. 252,300 | 7/1979 | Pryor | D6/20 |
| D. 260,816 | 9/1981 | Zissimopoulos | D24/31 |
| 1,490,650 | 4/1924 | Wagner | 248/412 X |
| 1,970,624 | 8/1934 | Recker | 248/412 |
| 2,283,324 | 5/1942 | Faber | 248/188.7 X |
| 2,346,274 | 4/1944 | Raven | 248/121 |
| 2,975,999 | 3/1961 | Bunch | 248/121 |
| 3,186,561 | 6/1965 | Strässle | 248/188.7 |
| 3,236,485 | 2/1966 | Staples | 248/188.7 X |
| 3,285,554 | 11/1966 | Voelkerding | 248/121 |
| 3,865,341 | 2/1975 | Fortnam et al. | 248/412 X |
| 4,653,710 | 3/1987 | Dickison | 248/188.7 |
| 4,744,536 | 5/1988 | Bancalari | 248/125 |
| 4,807,837 | 2/1989 | Gawlik et al. | 248/125 |
| 4,892,279 | 1/1990 | Lafferty et al. | 248/125 |
| 5,011,104 | 4/1991 | Fang | 248/412 X |

Primary Examiner—Alvin C. Chin-Shue
Assistant Examiner—Derek J. Berger
Attorney, Agent, or Firm—Patula & Associates

[57] ABSTRACT

A portable, intravenous support stand comprised of a lightweight, rigid material having a base support comprised of a plurality of legs releasably secured to a central base support by a tongue and groove type lock means, and a plurality of telescoping tubular members releasably secured to said base support by a base tubular member, hanger means incorporated into the uppermost portion of the top tubular member for supporting an intravenous container support arm, and a combination lock and stop means to lock the tubular members into place when adjusted for the desired height while stopping extension of the tubular members to prevent disassembly upon extension.

7 Claims, 2 Drawing Sheets

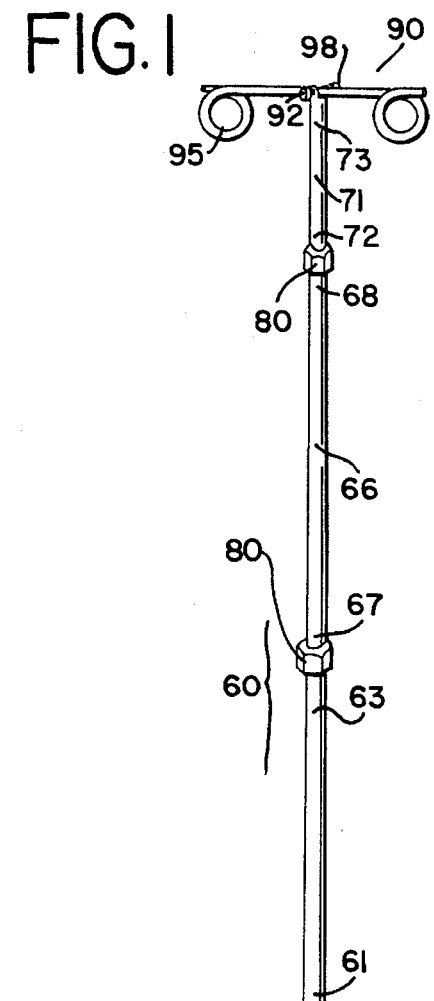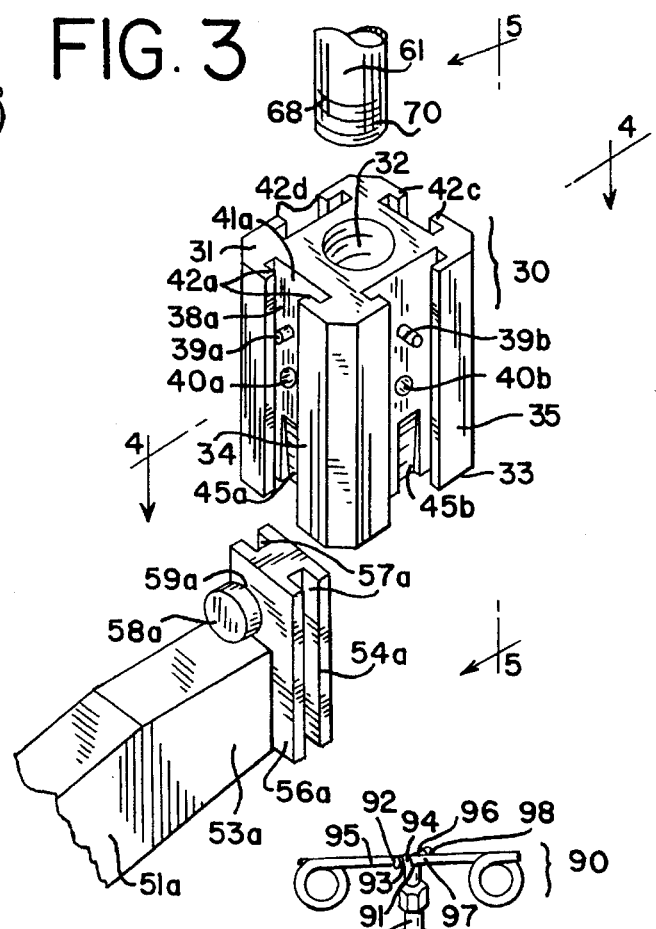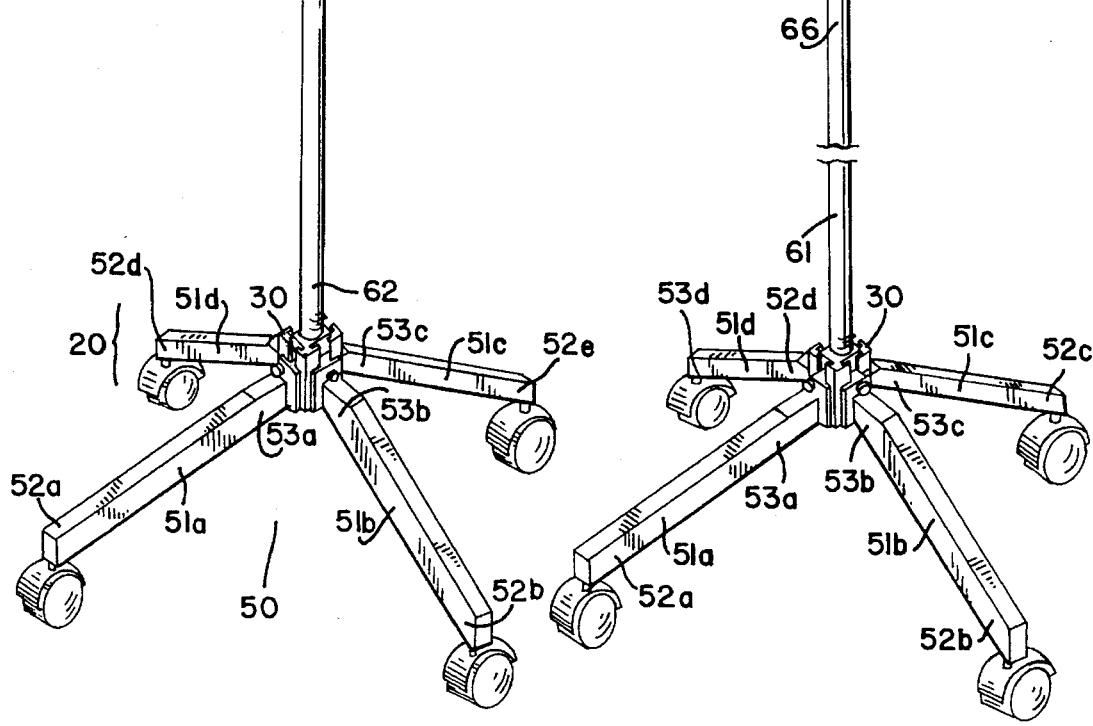

PORTABLE INTRAVENOUS SUPPORT STAND

This invention relates to pole-type stands for supporting intravenous fluid containers used to administer medicines and other aqueous solutions intravenously and, more particularly, to portable stands adapted for easy transportability and height adjustability to accomodate a variety of users.

BACKGROUND OF THE INVENTION

The spiraling costs of health care have necessitated alternatives to hospital visitation, creating a distinct need for products which are adaptable for home health care or other health care settings outside of professional health care institutions like hospitals. One such class of products is the intravenous support stand. A variety of portable intravenous stands have been developed to address home health care needs. For example, U.S. Pat. No. 4,892,279 to Lafferty and Howard teaches a portable medical intravenous equipment stand having a triple-sectioned telescoping pole-type assembly to allow for height adjustment, along with lock means to secure the stand to the desired height after adjustment.

The lock means disclosed in U.S. Pat. No. 4,892,279 is comprised of an internal rotary cam-clutch which locks the telescoping mast assembly in place when adjusted to the desired height. A seal and check valve located in the lower mast portion is disclosed to provide a pneumatic piston to inhibit the sudden fall of the upper mast segments. Additionally, the device is designed to be collapsible, with a single movement of a control handle provided to fold out or in the support legs to open or close the device for use or storage, respectively. The support legs are connected and hinged to a base plate of this invention. They are not designed to be separated from the telescoping mast assembly by the user, as is the case with the present invention.

Another portable intravenous stand is disclosed in U.S. Pat. No. 4,744,536 to Bancalari, which also teaches a telescoping height adjustable pole-type stand. In U.S. Pat. No. 4,744,536, the device is comprised of a pole having telescoping pole-type segments supported by a central base hub from which support legs are foldably mounted and hinged to allow for collapse and storage of the device when not in use. U.S. Pat. No. 4,744,536 teaches the use of retainer members to secure the pole segments in their chosen extended position, which retainer members loosen to allow for movement of the pole segments, and tighten to fix the segments to the desired device height.

U.S. Pat. No. 4,807,837 to Gawlik, Hoyt and Anderson also describes a collapsible pole-type medication support stand having telescoping pole members that lock to secure a chosen height adjustment, and a preferred leg assembly which complements the transportability of the device. As with U.S. Pat. Nos. 4,892,279 and 4,744,536, the design of U.S. Pat. No. 4,807,837 is a combination of telescoping pole-type segments and foldable support legs which are collapsed without disconnecting them from the device. In U.S. Pat. No. 4,807,837, the support legs are stored within the bottom section of tubing when the device is not in use, then extended from out of the bottom tubing and unfolded into a tripod configuration when in use. U.S. Pat. No. 4,807,837 also discloses lock means consisting of a knurled nut working in combination with threaded tube sections and a split beveled ring for fixing the tube segments to the desired height when the nut is tightened, or loosening the tubes for telescoping effect and height adjustment when tile nut is untightened.

In each of the patents referenced above, the features of portability, height adjustment, leg support mechanisms, lock mechanisms to secure the chosen height adjustment, and support members from which medicine to be administered is hung from the stand are variously addressed in efforts to provide improved portable intravenous support stands. In particular, the prior art referenced above teaches collapsible intravenous pole-type support stands, addressing various ways for collapsing the leg supports for the stand into a storage or use position. One problem with these types of intravenous supports is the relatively complicated machining and comlexity of parts which requires comparatively costly manufacturing resources and, consequently, reduced availability. Another problem with the collapsible, telescoping intravenous supports disclosed by the prior art is inadequate support stand strength. In Gawlik, et al., for example, a portable, light weight, collapsible I.V. stand is disclosed, but what the design gains in portability it loses in stability. For other collapsible, telescoping intravenous pole-type supports, collapsibility without disassembly is convenient, but generally bulkier to store when not in use.

The present invention improves upon the problems of the prior art of telescoping pole-type intravenous support stands. One object of the present invention is to provide a disassemblable pole-type, telescoping intravenous support stand which is lightweight and portable to allow for easy disassembly and storage when not in use, yet is very stable.

Another object of the invention is to provide a telescoping pole-type intravenous support stand which is mechanically streamlined in design to allow for lower cost manufacturing, including a support stand which is free of hinges, collapse levers or the like intended to automate collapsibility of the device.

Another object of the invention is to provide a pole-type intravenous support stand having telescoping tubular members with combination lock and stop extension means to allow for variable height adjustment that can be locked in place without over-extension of the tubular members upon attempting to increase the stand height which otherwise would result in disassembly of the tubular members.

Still another object of the invention is to provide a pole-type intravenous support stand having combination collapsible and disassemblable features, with telescoping tubular members being capable of collapsing within one another for height adjustment and easy, efficient storage, and base support and intravenous container support arms being disassemblable from the telescoping tubular members also for easy, efficient storage, preferably by tongue and groove machined releasable lock fit.

Another object of the invention is to provide a pole-type intravenous support stand which is simple to operate yet flexible in its range of use to allow for the mechanically unsophisticated to use the support device outside of the professional setting, such as a hospital or similar institutional environment and, in particular, to use the device in the home health care setting.

BRIEF SUMMARY OF THE INVENTION

The present invention is a portable, intravenous support stand comprised of a lightweight yet rigid material having a base support defined by a plurality of legs releasably secured to a central base support by a tongue and groove type lock means, and a plurality of telescoping tubular members which collapse into the base tubular member, which base tubular member is releasably secured to said base support. The device is further defined by hanger means incorporated into the uppermost portion of the top tubular member for receiving and releasably locking into place an intravenous container support arm, and a combination lock and stop means to lock the tubular members into place when adjusted for the desired height while stopping extension of the tubular members to prevent them from pulling apart and disassembling by over-extending the height adjustment of the device.

BRIEF DESCRIPTION OF THE DRAWINGS

FIG. 1 is a perspective view of the invention extended out to a desired height.

FIG. 2 is a perspective view of the invention partially collapsed to a reduced height relative to that depicted in FIG. 1.

FIG. 3 is an exploded partial perspective view of the central base support and the channel end of one support leg which locks into the central base support for assembly of the base support of the device.

DETAILED DESCRIPTION OF THE DRAWINGS

Figure 4:
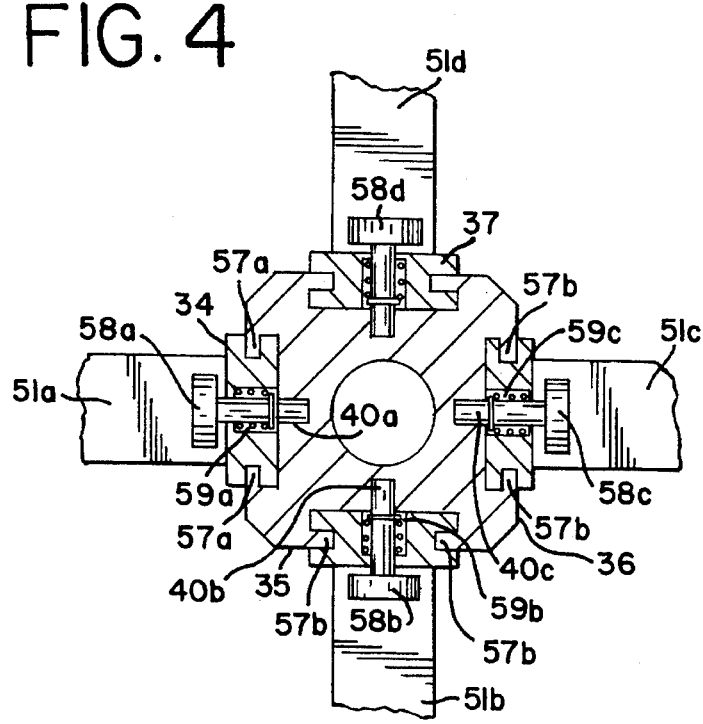
FIG. 4 is a cross-sectional view of the central base support with support legs connected, taken along line 4—4 of FIG. 3.

The objects of the present invention, its advantages and other aspects will be apparent upon consideration of the following detailed description of the invention. This detailed description is intended to disclose the invention by way of example through preferred embodiments, and is not intended to limit the spirit and scope of the invention.

Referring now to FIG. 1, the device 10 of the present invention is depicted in perspective view, showing the base support means 20, vertical support means 60, lock and stop means 80 and hanger means 90. The base support means 20 is comprised of central base support 30 which, in the preferred embodiment of the invention, as shown more clearly in FIG. 3, has a top end 31, a central bore 32 internally threaded for receiving vertical support means 60 at said top end 31, a bottom end 33, sides 34, 35, 36, and 37, and leg support means 50. For purposes of this detailed description, the component parts of the central base support 30 and leg support means 50 will be disclosed with reference to one side and leg only, as shown in FIG. 3. Letters "a" through "d" after each component part number are used to designate like parts on each of said sides 34, 35, 36 and 37, even though separate descriptions for parts a–d are not repeated throughout because these would be functionally identical.

Referring now to FIG. 3, central base support 30 is comprised of sides 34, 35, 36 and 37, each having a leg lock channel 38a, 38b, 38c, and 38d, respectively, formed as a continuous vertical T- slot type groove into said sides 34, 35, 36 and 37. As noted above, each component part of base support means 20 and leg support means 50 applies four times, a–d, one for each of the four sides 34, 35, 36, and 37, of said central base support 30 even though letter designations are omitted hereafter. Leg lock channel 38 is further defined by a channel groove face 41 and a channel stop pin 39 protruded from said channel groove face 41. Said central base support 30 is further defined by channel lock pin recess 40 formed integrally on said channel groove face 41 below channel stop pin 39. Leg lock channel 38 is also further defined by a set of channel groove flanges 42 integrally formed along the longitudinal perimeter of said leg lock channel 38.

Leg support means 50 cooperatively associate with said central base support 30 to achieve a disassemblable base support 20 which releasably lock fits said central base support 30 with said leg support means 50. Leg support means 50 is comprised of a plurality of legs which, in the preferred embodiment of the invention, is four legs 51a, 51b, 51c and 51d, each of said legs 51 having a wheel end 52 and a channel end 53. In the preferred embodiment of the invention, said wheel end 51 is adapted to receive conventional wheel-type casters to provide for mobility of the device 10 when assembled. Said channel end 53 is defined by a channel guide 54 formed into a modified wide-flanged H-beam type configuration, said channel guide 54 having an interior guide member 55, an exterior guide member 56, and a pair of groove flange channels 57 which cooperatively associate with leg lock channel 38 by receiving said set of channel groove flanges 42 to be thereby secured between said interior guide member 55 and said exterior guide member 57 of channel guide 54. Said channel guide 54 is further defined by a bore 59 formed through said interior guide member 55 and exterior guide member 56, which bore 59 is generally perpendicular to said guide members 55 and 56, and is adapted to receive spring-actuated tension pin 58 which is mounted therewithin to protrude retractably from said interior guide member 55.

To mount said leg 51 within said leg lock channel 38 of said central base support 30, said interior guide member 55 is inserted into said leg lock channel 38 at said bottom end 33 of central base support 30, with said interior guide member 55 being generally coplanar with said channel groove face 41. Tension pin 58 then is drawn back toward said wheel end 52 of said leg 51 until pin 58 is flush with the plane of interior guide member 55. Channel guide 54 then is slid further into said leg lock channel 38 toward said top end 31 until pin 58 hits said channel lock pin recess 40, at which time the spring-actuated means of tension pin 58 force pin 58 to protrude beyond interior guide member 55 and into said recess 40, with channel guide 54 further locked into place by channel stop pin 39 which prevents said channel guide 54 of leg 51 from advancing any further upward within said leg lock channel 38. These steps are repeated for the remaining three legs 51 of leg support means 50 to assemble the base support means 20. Disassembly is similary achieved by drawing back tension pin 58 to a position flush with the face of interior guide member 55, then sliding said channel guide 54 away from channel stop pin 39 toward said bottom end 32 and out of said leg lock channel 38.

Figure 5:
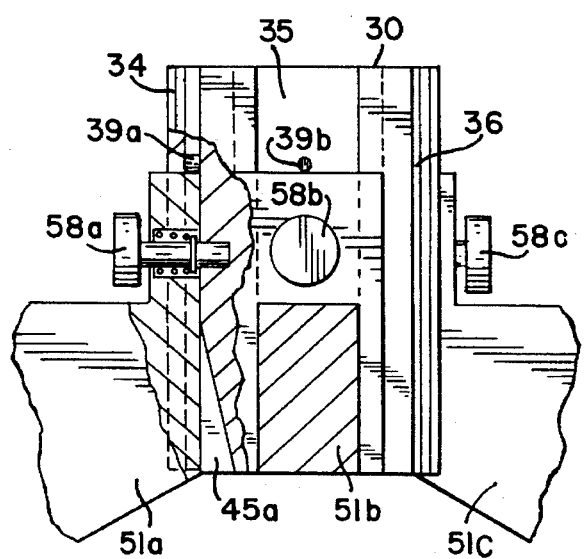
FIG. 5 is a side elevational partial cross-sectional view of the invention taken along line 5—5 of FIG. 3.
Figure 7:
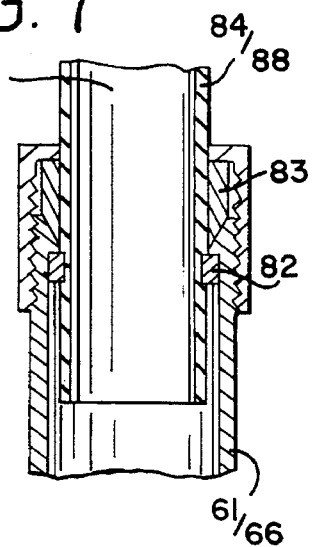
FIG. 7 is a side elevational view of the lock and stop means of the present invention as engaged.

FIGS. 4 and 5 further depict the disassemblable base support means 20. FIG. 4 is a top cross-sectional view of central base support 30 and partial top cross-sectional view of leg support means 50, showing the four sets of legs 51 at channel end 53, with tension pin 58 locked into channel lock pin recess 40 within leg lock channel 38. FIG. 5 is a side elevational, partial cutaway view of said central base support 30 with legs 51 locked into place within said leg lock channels 38, also showing tension pin 58 in its actuated, locked position within said channel lock recess 40, and further showing channel stop pin 39 preventing further advancement of said channel guide 54 upward within said leg lock channel 38. FIG. 5 also depicts an alternate embodiment of the present invention through slot lock guide 45 which is an angular groove integrally formed within said central base support 30 beginning just below said recess 40 and reaching its maximum angle dimension at said bottom end 33, said slot lock guide 45 adapted to slidably receive said tension pin 58 to implement locking and assembly of said leg support means 50 from said central base support 30 by urging said tension pin 58 toward said recess 40.

FIGS. 1 and 2 depict the vertical support means 60 of the device 10 comprised of a plurality of tubular members 61, 66 and 76. Said tubular member 61 is the base tube having the largest diameter, preferably approximately one inch. Tubular member 61 has an externally threaded first end 62 adapted to cooperatively associate with said central bore 32 of said central base support 30 for mounting said tubular member 61 therewithin. Tubular member 61 also has a plurality of slots 64 milled at said second end 63 to facilitate locking of the lock and stop means 80, and threads 65 formed integrally on the outside perimeter of second end 63.

Figure 6:
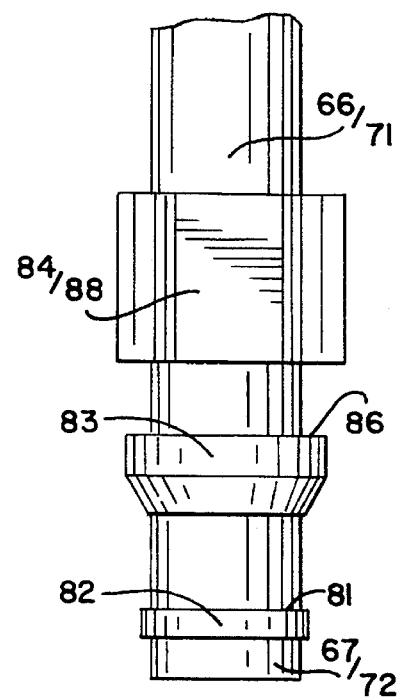
FIG. 6 is a side elevational partial view of the lock and stop means of the present invention as disengaged.

Tubular member 66 is the middle tubular member of the vertical support means 60, having the second largest diameter, preferably approximately ⅞ inch. Tubular member 66 has a first end 67 which is slidably and extendably retained within tubular member 61 from said second end 63, and a second end 68 having slots 69 and threads 70 formed integrally on the outside perimeter of said second end 68. Tubular member 66 is further defined by an external perimeter machine groove 81 located on the outside perimeter of tubular member 66 near said first end 67 and adapted to retain stop ring 82, as depicted in FIG. 6, while at the same time allowing said stop ring 82 to create a stop ridge 86 which is slightly larger in diameter than tubular member 66.

Vertical support means 60 is further comprised of tubular member 71 which is the top most tubular member 66 of the vertical support means 60, having the smallest diameter of vertical support means 60, preferably approximately ¾ inch. Tubular member 71 has a first end 72 which is slidably and extendably retained within tubular member 66 from said second end 68, and a second end 73 supporting hanger means 90, said hanger means 90 comprised of an intravenous support arm channel 91 integrally formed at said second end 73, channel walls 94 and 96 also integrally formed at said second end 73 of tubular member 71 and defining said support arm channel 91 therebetween, bore 93 integrally formed through channel wall 94 and adapted to receive set screw 92 which is threaded through bore 93, and bore 97 integrally formed through channel wall 96 and adapted to receive set screw 98 which is threaded through bore 97. Intravenous support arm 95 rests within channel 91 and is secured therein when set screws 92 and 98 are tightened to force support arm 95 snugly against said set screws 92 and 98 within channel 91, as shown in FIGS. 1 and 2. Alternatively, hanger means 90 may be comprised of only one bore 93 which forces support arm 95 against channel wall 96 when set screw 92 is tightened. Tubular member 71 is further defined by an external perimeter machine groove 81 located near said first end 72 and adapted to retain stop ring 82, as depicted in FIG. 6, while at the same time allowing said stop ring 82 to create a stop ridge 86 which is slightly larger in diameter than tubular member 71.

The device 10 of the present invention is further defined by lock and stop means 80, shown in FIGS. 1, 2, 6 and 7. Lock and stop means 80 is comprised of stop ring 82, capped ring 83, locking nut 84 to lock tubular member 66 with tubular member 61, and locking nut 88 to lock tubular member 71 with tubular member 66. Locking nuts 84 and 88 are internally threaded and adapted to mate with external tube threads 65 of tubular member 61 and external tube threads 70 of tubular member 66, respectively. In the preferred embodiment of the invention, capped ring 83 is slidably positioned on the exterior of tubular member 66 near said first end 67 but above said stop ring 82 and below said locking nut 84. Said first end 67 of tubular member 66 is inserted within said second end 63 of tubular member 61 and adjusted to the desired height, at which point locking nut 84 is slid downward until it engages threads 65 of tubular member 61, thereby seating capped ring 83 within said locking nut 84. Capped ring 83 abuts stop ridge 86 to provide the stop means of the lock and stop means 80 and to prevent further extension of tubular member 66 outside of tubular member 61, thereby preventing potentially hazardous disassembly of the vertical support means 60 through over-extension of the tubular member 66 from tubular member 61.

Likewise, a second capped ring 83 is slidably positioned on the exterior of tubular member 71 near said first end 72 but above said stop ring 82 and below said locking nut 88. Said first end 72 of tubular member 71 is inserted within said second end 68 of tubular member 66 and adjusted to the desired height, at which point locking nut 88 is slid downward until it engages threads 70 of tubular member 66, thereby seating capped ring 83 within said locking nut 88 and preventing further extension of tubular member 71 outside of tubular member 66. Capped ring 83 also abuts stop ridge 86 to provide the stop means of the lock and stop means 80, thereby preventing potentially hazardous disassembly of the vertical support means 60 through over-extension of the tubular member 71 from tubular member 66. Although locking nuts 84 and 88 are depicted in the drawings at FIGS. 1 and 2 as hexagonal nuts, any conventional external locking nut configuration, such as a knurled nut, may be employed.

What is claim is:

1. A movable pole-type support stand, comprising in combination:

base support means having a central base support and support means releasably affixed to said central base support, vertical support means releasably connected to rise from said base support means, said vertical support means being height adjustable;

lock and stop means integrated into said vertical support means to releasably set height adjustment and prevent over-extension of said vertical support means;

hanger means incorporated into the uppermost portion of said vertical support means for supporting materials, said hanger means being comprised of a first and second channel wall integrally formed on said second end of the top most portion of said vertical support means, said first and second channel walls forming a support arm channel therebetween, said hanger means further defined by said first channel wall having a bore through which a support set screw is threaded, and a support arm removably cradled within said support arm channel and fixedly secured therewithin upon tightening said support set screw to bear down through said bore onto said support arm within said support arm channel and against said second channel wall.

2. The stand recited in claim 1, wherein said hanger means is comprised of a first and second channel wall integrally formed on said second end of the top most portion of said vertical support means, said first and second channel walls forming a support arm channel therebetween, said hanger means further defined by said first and second channel walls each having a bore disposed on a common axis and through which a support set screw is threaded, and a support arm removably cradled within said support arm channel and fixedly secured therewithin upon tightening said support set screws to bear down through said bores onto said support arm within said support arm channel.

3. The stand recited in claim 1, wherein said central base support has a plurality of faces including a top end, bottom end, and at least three side walls, and wherein said leg support means is comprised of a plurality of legs numbering at least three, each of said legs having a wheel end having conventional caster-type wheels.

4. The stand recited in claim 3, wherein said sides and said legs numbers four.

5. An intravenous telescoping pole-type support stand, comprising:

base support means having a central base support and leg support means releasably affixed to said central base support; said central base support having a plurality of faces including a top end, bottom end, and at least three side walls, each of said side walls having a leg lock channel integrally formed along the vertical length of each of said side walls from said top end to said bottom end and having a channel groove face and a set of channel groove flanges defining the width of each of said leg lock channels, said central base support being further defined by a channel lock pin recess formed on said channel groove face of each of said sides, and having a channel stop pin integrally formed above said channel lock pin recess and protruding from each of said channel groove faces, and wherein said leg support means is comprised of a plurality of legs numbering at least three, each of said legs having a channel end and a wheel end having conventional caster-type wheels to mobilize said stand upon assembly, said channel end being comprised of a channel guide having an interior guide member and an exterior guide member being spaced apart from and generally coplanar with said interior guide member, said channel guide being further defined by a pair of groove flange channels formed between said interior and exterior guide members and adapted to cooperatively associate with said channel groove flanges of said leg lock channels of said side walls of said base support, said channel guide being further defined by a bore formed through said exterior and interior guide members and adapted to receive a spring actuated tension pin which protrudes beyond the face of said interior guide member when in its actuated position and is flush with the face of said interior member when drawn away from said exterior member to allow said channel guide to engage said leg lock channel;

vertical support means releasably connected to and rising from said base support means, said vertical support means being height adjustable and comprised of a plurality of tubular members each having a first end and a second externally threaded end and having lock and stop means integrated therewithin, said lock and stop means being comprised of an internally threaded locking nut adapted to releasably engage said externally threaded end, a capped ring positioned on the exterior of said second end of said tubular member and adapted to be seated within said locking nut, and a stop ring having a stop ridge, said stop ring positioned on the exterior of said first end of said tubular member to prevent over-extension of said tubular members by abutting said capped ring against said stop ridge upon releasably lock-engaging said locking nut with said externally threaded second end and thereby seating said capped ring within said locking nut;

hanger means located at said second end of the top most portion of said vertical support means for supporting articles held by said stand.

6. The stand recited in claim 5, wherein said leg lock channels are further defined by a milled slot lock guide integrally formed to angle inward from said channel groove face starting under said channel lock pin recess toward said central bore, said slot lock guide being of a width to receive said tension pin near said bottom end of said central base support and slidably urge said tension pin toward said channel lock pin recess for locking of said tension pin within said channel lock pin recess.

7. An improved portable intravenous support stand having telescoping vertical support tubular members comprised of a plurality of tubular members each having a first end and a second end, a base having a plurality of legs, and a hanger for supporting intravenous medication from the top of said stand, comprising;

said second end of said tubular members from which a smaller tubular member extends being externally threaded;

a combination lock and stop means integrated at said second end for each tubular member from which a smaller tubular member extends, said lock and stop means being comprised of an internally threaded locking nut adapted to releasably engage said externally threaded end, a capped ring positioned on the exterior of said second end of said tubular member and adapted to be seated within said locking nut, and a stop ring having a stop ridge, said stop ring positioned on the exterior of said first end of said tubular member to prevent over-extension of said tubular members by abutting said capped ring against said stop ridge upon releasably lock-engaging said locking nut with said externally threaded second end and thereby seating said capped ring within said locking nut;

releasable lock means for assembling and disassembling said base, wherein said releasable lock means is defined by said central base support having a plurality of faces including a top end, bottom end, and at least three side walls, each of said side walls having a leg lock channel integrally formed along the vertical length of each of said side walls from said top end to said bottom end and having a channel groove face and a set of channel groove flanges defining the width of each of said leg lock channels, said central base support being further defined by a central bore formed from said top end through to said bottom end and being internally threaded to receive said vertical support tubular members at said top end, and further having a channel lock pin recess formed on said channel groove face of each of said sides, and having a channel stop pin integrally formed above said channel lock pin recess and protruding from each of said channel groove faces; and wherein each of said legs has a channel end and a wheel end having conventional caster-type wheels, said channel end being comprised of a channel guide having an interior guide member and an exterior guide member being spaced apart from and generally coplanar with said interior guide member, said channel guide being further defined by a pair of groove flange channels formed between said interior and exterior guide members and adapted to cooperatively associate with said channel groove flanges of said leg lock channels of said side walls of said base support, said channel guide being further defined by a bore formed through said exterior and interior guide members and adapted to receive a spring actuated tension pin which protrudes beyond the face of said interior guide member when in its actuated position and is flush with the face of said interior member when drawn away from said exterior member to allow said channel guide to engage said leg lock channel.

* * * * *